United States Patent
Govari et al.

(10) Patent No.: US 11,406,307 B2
(45) Date of Patent: Aug. 9, 2022

(54) IMPEDANCE MEASUREMENTS USING BURST PULSES TO PREVENT NOISE ON ECG

(71) Applicant: Biosense Webster (Israel) Ltd., Yokneam (IL)

(72) Inventors: Assaf Govari, Haifa (IL); Yaron Ephrath, Karkur (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 136 days.

(21) Appl. No.: 16/230,654

(22) Filed: Dec. 21, 2018

(65) Prior Publication Data
US 2020/0196894 A1 Jun. 25, 2020

(51) Int. Cl.
*A61B 5/316* (2021.01)
*A61B 5/053* (2021.01)
*A61B 5/00* (2006.01)
*A61B 5/25* (2021.01)

(52) U.S. Cl.
CPC ............. *A61B 5/316* (2021.01); *A61B 5/053* (2013.01); *A61B 5/25* (2021.01); *A61B 5/7203* (2013.01); *A61B 5/0006* (2013.01); *A61B 5/6823* (2013.01)

(58) Field of Classification Search
CPC . A61B 5/0006; A61B 5/04017; A61B 5/0408; A61B 5/053; A61B 5/6823; A61B 5/7203; A61B 5/25; A61B 5/316
See application file for complete search history.

(56) References Cited

U.S. PATENT DOCUMENTS

| 3,495,584 A | * | 2/1970 | Schwalm | A61B 5/276 600/508 |
| 3,757,778 A | * | 9/1973 | Graham | A61B 5/276 600/508 |
| 4,917,099 A | * | 4/1990 | Stice | G01R 17/105 600/509 |
| 4,993,423 A | * | 2/1991 | Stice | G01R 17/105 600/509 |

(Continued)

FOREIGN PATENT DOCUMENTS

| WO | WO2009036313 A1 | 3/2009 |
| WO | WO2014051590 A1 | 4/2014 |

OTHER PUBLICATIONS

European Search Report for corresponding EPA No. 19217937.2 dated May 26, 2020.

*Primary Examiner* — Christopher A Flory
(74) *Attorney, Agent, or Firm* — Volpe Koenig

(57) ABSTRACT

A system and method for measuring the impedance of one or more of a plurality of leads in an electrocardiogram (ECG) are disclosed. These may include applying a plurality of leads to a patient's body, applying a plurality impedance pads to the patient's body, providing a burst pulse from the catheter electrode of the ECG, measuring impedance signals across ones of the plurality of impedance pads and the plurality of leads, and determining the impedance for one or more leads from the measured impedance signals. The plurality of impedance pads may define a first axis from the right side of the patient's chest to the left side of the patient's chest, a second axis from the upper chest area of the patient to the lower abdomen area of the patient, and a third axis from the center of the patient's back to the center of the patient's chest.

17 Claims, 4 Drawing Sheets

(56) References Cited

U.S. PATENT DOCUMENTS

| | | | | |
|---|---|---|---|---|
| 5,287,859 A * | 2/1994 | John | A61B 5/377 | 600/544 |
| 5,511,553 A * | 4/1996 | Segalowitz | A61B 5/0006 | 600/508 |
| 5,564,429 A * | 10/1996 | Bornn | G16H 40/67 | 600/508 |
| 5,704,365 A * | 1/1998 | Albrecht | A61B 5/222 | 600/515 |
| 5,792,194 A * | 8/1998 | Morra | A61B 5/0538 | 607/122 |
| 6,044,294 A * | 3/2000 | Mortazavi | A61N 1/36521 | 600/547 |
| 6,050,267 A * | 4/2000 | Nardella | A61B 5/0536 | 128/899 |
| 6,223,073 B1 * | 4/2001 | Seegobin | A61B 5/35 | 600/515 |
| 6,269,264 B1 * | 7/2001 | Weyant | A61N 1/36521 | 600/547 |
| 7,570,989 B2 * | 8/2009 | Baura | A61B 5/364 | 600/513 |
| 8,887,736 B2 * | 11/2014 | Markowitz | A61B 5/0422 | 128/899 |
| 2002/0165458 A1 * | 11/2002 | Carter | A61B 5/0006 | 600/509 |
| 2003/0073916 A1 * | 4/2003 | Yonce | A61B 5/30 | 600/509 |
| 2003/0083584 A1 * | 5/2003 | Yonce | A61B 5/276 | 600/509 |
| 2006/0206024 A1 * | 9/2006 | Weeks | A61B 5/282 | 600/418 |
| 2006/0241384 A1 * | 10/2006 | Fisher | A61B 5/0013 | 600/414 |
| 2008/0154143 A1 * | 6/2008 | Xue | A61B 5/341 | 600/509 |
| 2009/0076345 A1 * | 3/2009 | Manicka | A61B 5/6833 | 600/301 |
| 2009/0076363 A1 * | 3/2009 | Bly | A61B 5/30 | 600/372 |
| 2009/0157337 A1 * | 6/2009 | Zhang | A61B 5/318 | 702/65 |
| 2009/0264746 A1 * | 10/2009 | Markowitz | A61B 5/066 | 600/424 |
| 2009/0299432 A1 * | 12/2009 | Stadler | A61N 1/36521 | 607/28 |
| 2010/0114204 A1 * | 5/2010 | Burnes | A61N 1/37 | 607/4 |
| 2010/0125305 A1 * | 5/2010 | Bornzin | A61N 1/36521 | 607/8 |
| 2010/0179421 A1 | 7/2010 | Tupin | | |
| 2010/0324612 A1 * | 12/2010 | Matos | A61N 1/0492 | 607/4 |
| 2011/0066050 A1 * | 3/2011 | Moon | A61B 5/1116 | 600/509 |
| 2011/0190642 A1 * | 8/2011 | Alt | A61N 1/3601 | 600/484 |
| 2011/0213260 A1 * | 9/2011 | Keel | A61B 5/686 | 600/513 |
| 2012/0108920 A1 * | 5/2012 | Bly | A61B 5/0537 | 600/306 |
| 2014/0249442 A1 * | 9/2014 | Banet | A61B 5/0022 | 600/526 |
| 2014/0249443 A1 * | 9/2014 | Banet | A61B 5/0816 | 600/526 |
| 2015/0374256 A1 * | 12/2015 | Skrabal | A61B 5/04082 | 600/301 |
| 2016/0203608 A1 * | 7/2016 | Izmirli | G16H 30/20 | 382/128 |
| 2016/0274162 A1 * | 9/2016 | Freeman | A61N 1/39 | |
| 2016/0354041 A1 * | 12/2016 | Gore | A61B 5/0531 | |
| 2017/0143265 A1 * | 5/2017 | Hallberg | A61B 5/25 | |
| 2017/0238812 A1 * | 8/2017 | Atlas | A61B 5/0205 | |
| 2018/0098739 A1 * | 4/2018 | Freeman | A61M 16/026 | |
| 2018/0132753 A1 * | 5/2018 | Schweitzer | A61B 5/7264 | |
| 2018/0184933 A1 * | 7/2018 | Sullivan | A61N 1/3925 | |
| 2018/0214079 A1 * | 8/2018 | Banet | A61B 5/0531 | |
| 2018/0280646 A1 * | 10/2018 | Freeman | A61M 16/0003 | |
| 2020/0000355 A1 * | 1/2020 | Khair | A61B 5/0006 | |
| 2020/0329977 A1 * | 10/2020 | Freeman | A61B 5/7203 | |

* cited by examiner

IMPEDANCE MEASUREMENTS USING BURST PULSES TO PREVENT NOISE ON ECG

FIELD OF INVENTION

The present invention is related to electrocardiography, referred to herein as ECG, and may also be referred to as EKG. More particularly, the present invention is related to impedance measurements using burst pulses to prevent noise on ECG.

BACKGROUND

Currently, electrocardiography, referred to herein as ECG, and may also be referred to as EKG, is effected by the impedance of the patient's body, of the contact to connect the probes to the patient's body, and from the connections themselves. In order to understand and read the ECG, this impedance needs to be accounted for. When physicians use an ECG to study heart activity, an accounting for the impedance needs to occur in order to effectively isolate the electrical signals from the heart. Previous attempts to determine the impedance have been made using frequency multiplexing. In these frequency multiplexing attempts, other frequencies are used to measure the impedance. These other frequencies are generally high frequency and do not interfere with the measurements of the electrical signals from the heart. However, the significantly different frequencies used effects the accuracy of the measurements of the impedance. That is, the response may vary based on the frequency of the signal, and because of the difference in frequency, frequency multiplexing, tends to affect the accuracy. Therefore, a need exists to provide improved methods of measuring the impedance so that the effects of such impedance may be removed from the ECG study thereby allowing the electrical signals of the heart to be discerned more clearly.

BRIEF DESCRIPTION OF THE DRAWINGS

A more detailed understanding may be had from the following description, given by way of example in conjunction with the accompanying drawings wherein.

DETAILED DESCRIPTION

Figure 1:
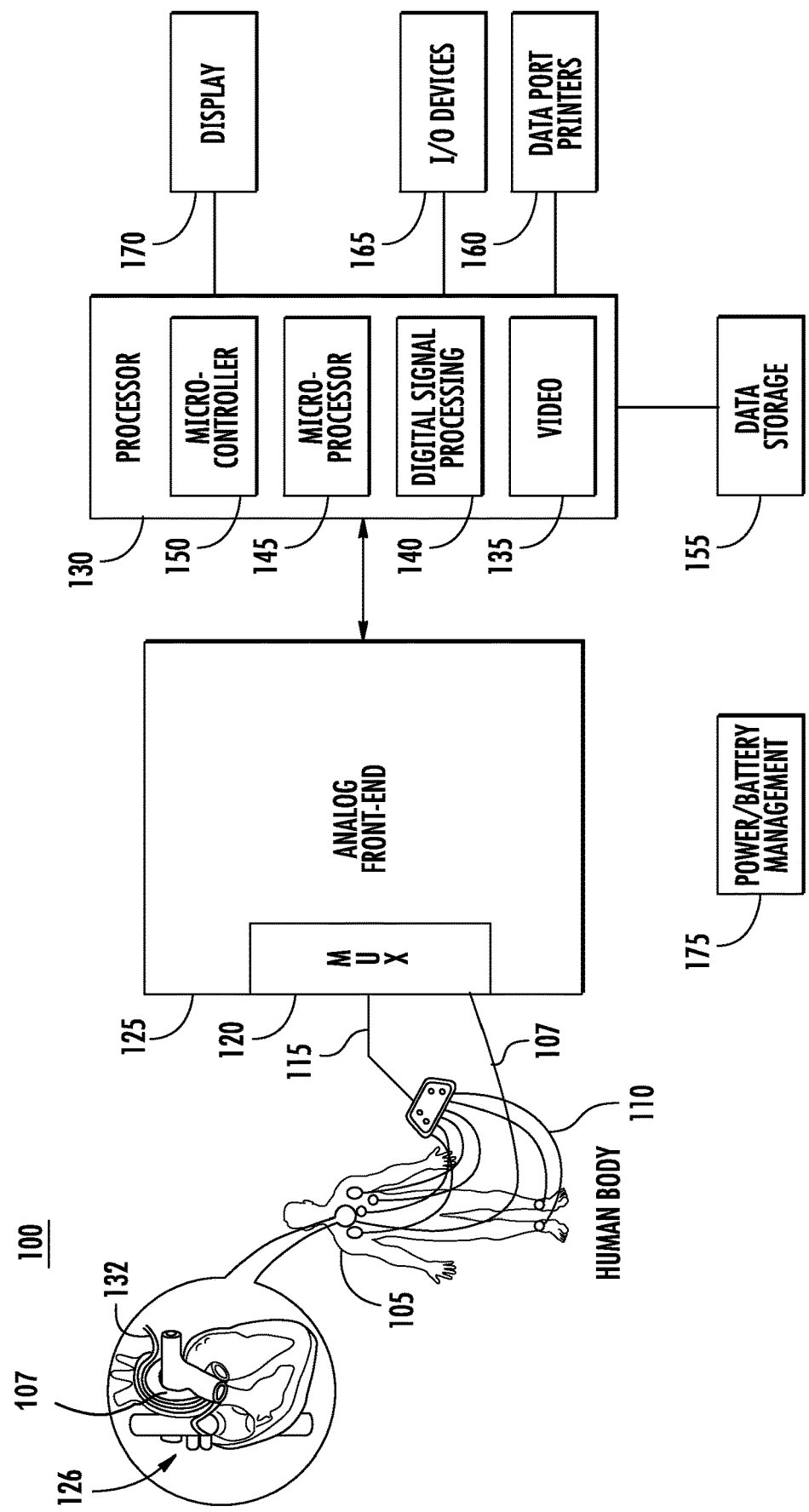
FIG. 1 illustrates a block diagram of an ECG device for performing impedance measurements using burst pulses to prevent noise.

Electrocardiography, referred to herein as ECG, and may also be referred to as EKG, is the process of recording the electrical activity of the heart over a period of time using electrodes placed on the skin, or inside the heart using a specialized catheter (i.e. intracardiac ECG). These electrodes detect the small electrical changes that arise from the heart muscle's electro-physiologic pattern of depolarizing during each heartbeat. ECGs are commonly or routinely performed cardiology tests.

An intracardiac electrogram (ICEG) is an ECG with some added intracardiac leads (that is, inside the heart). Such an electrogram may be utilized in combination with, or in the alternative to, a conventional 12-lead ECG. In a conventional 12-lead ECG, 10 electrodes are placed on the patient's limbs and on the surface of the chest. The overall magnitude of the heart's electrical potential is then measured from 12 different angles ("leads") and is recorded over a period of time. The procedure duration may vary from tens of minutes to several hours. During each procedure usually there are several dozens of ablation sessions, each of which last several seconds up to approximately 1 minute, for example. By way of example, a conventional 12-lead ECG may be performed over a period of time, such as 10 seconds, for example. In this way, the overall magnitude and direction of the heart's electrical depolarization is captured at each moment throughout the cardiac cycle. A graph of voltage versus time produced by this medical procedure is referred to as an electrocardiogram.

During each heartbeat, a healthy heart has an orderly progression of depolarization. This orderly pattern of depolarization gives rise to the characteristic ECG tracing. To the trained clinician, an ECG conveys a large amount of information about the structure of the heart and the function of its electrical conduction system. Among other things, an ECG can be used to measure the rate and rhythm of heartbeats, the size and position of the heart chambers, the presence of any damage to the heart's muscle cells or conduction system, the effects of cardiac drugs, and the function of implanted pacemakers. Interpretation of the ECG is fundamentally about understanding the electrical conduction system of the heart. Normal conduction starts and propagates in a predictable pattern, and deviation from this pattern can be a normal variation or be pathological.

However, in order to ascertain the signals from the electrical conduction system of the heart, the measured signals need to be filtered to remove any unwanted and spurious signals or noise.

A system and method for measuring the impedance of one or more of a plurality of leads in an electrocardiogram (ECG) are disclosed. The system and method may include applying a plurality of leads to a patient's body, applying a plurality impedance pads to the patient's body, providing a burst pulse from the catheter electrode of the ECG, measuring impedance signals across ones of the plurality of impedance pads and the plurality of leads, and determining the impedance for one or more leads from the measured impedance signals. The plurality of impedance pads defines a first axis from the right side of the patient's chest to the left side of the patient's chest. The plurality of impedance pads defines a second axis from the upper chest area of the patient to the lower abdomen area of the patient. The plurality of impedance pads defines a third axis from the center of the patient's back to the center of the patient's chest. The plurality of leads includes a standard 12-lead ECG including three limb leads, three augmented limb leads arranged in a spoke fashion in the coronal plane, and six precordial leads configured on the perpendicular traverse plane.

The system and method may alternatively include applying a plurality of leads to a patient's body and measuring impedance signals across paired ones of the plurality of the plurality of leads during periods between ECG measurements. The plurality of leads includes a standard 12-lead ECG including three limb leads, three augmented limb leads arranged in a spoke fashion in the coronal plane, and six precordial leads configured on the perpendicular traverse plane. The plurality of leads is each paired to an adjacent one of the plurality of leads.

The system for performing an ECG and measuring impedance includes a plurality of leads for attaching to a subject in order to capture electric signals, a signal processor to process the captured electrical signals, and an output device to output the process captured electrical signals, wherein the impedance of the measurements is monitored and the signal processor removes the impedance from the process captured electrical signals. The system may include a plurality of impedance pads configured to provide impedance information for the measurements. A catheter electrode may provide a burst pulse to enable the measurement of the impedance information. The system may alternatively measure the impedance information across pairs of the plurality of electrodes.

FIG. 1 illustrates a block diagram of a device 100 in which the impedance measurements using burst pulses may be utilized. Device 100 may take the form of an ECG machine. Device 100 includes a series of leads 110 that taper into a single multiplexed input 115. The series of leads 110 may be placed on a human test subject 105. Additional leads 107, which may be included with series of leads 110, or separate therefrom (as shown) may be intracardiac leads 107.

Intracardiac leads 107 may be used for diagnostic or therapeutic treatment, such as for mapping electrical potentials in a heart 126 of a patient 105. Alternatively, intracardiac leads 107 may be used, mutatis mutandis, for other therapeutic and/or diagnostic purposes in the heart or in other body organs.

Intracardiac leads 107 may be inserted in the vascular system of the patient 105 so that a distal end 132 of the leads 107 enters a chamber of the patient's heart 126. Although FIG. 1 shows a single lead 107 with a single location sensor, embodiments of the present invention may utilize probes with more than one location sensor.

The signals on the series of leads 110 are input into an analog front-end 125 via an input multiplexor 120. The analog front-end 125 provides to, and is controlled by, a processor 130. Processor 130 may include, as shown, a video controller 135, digital signal processor 140, a microprocessor 145, and a micro controller 150. Processor 130 is coupled to a data storage 155. Data ports and printers 160 may be coupled to processor 130. Other input/output devices 165 may be coupled to processor 130. A display 170 may be used to provide output of the signals of the ECG. A power/battery management system 175 may be included to provide power for device 100 to operate.

Series of leads 110 includes both the generally used forms of electrodes and may also include leads used for ECG procedures. Each of the series of leads 110 may include a conductive pad in contact with the body 105 that makes an electrical circuit with the electrocardiograph. On a standard 12-lead ECG there are only 10 leads 110. Series of leads 110 may be grouped into three sets: limb, augmented limb, and precordial. Generally, the 12-lead ECG has a total of three limb leads and three augmented limb leads arranged like spokes of a wheel in the coronal plane (vertical) and six precordial leads that lie on the perpendicular transverse plane (horizontal).

Analog front-end 125 receives the signals from the series of leads 110 and performs analog processing, such as filtering, of the signals.

Data storage 155 is any device that records information. Data storage may provide a storage medium for the signals includes within device 100 and a place for calculations of processor 130 to be stored.

Microprocessor 145 may be a computer processor which incorporates the functions of a computer's central processing unit (CPU) on a single integrated circuit (IC), or a few integrated circuits. Microprocessor 145 may be a multipurpose, clock driven, register based, programmable electronic device which accepts digital or binary data as input, processes it according to instructions stored in its memory or data storage 155, and provides results as output. Microprocessor 145 contains both combinational logic and sequential digital logic.

Micro controller 150 may be one or more small computers on a single integrated circuit. Micro controller 150 may contain one or more CPUs along with memory and programmable input/output peripherals. Program memory in the form of Ferroelectric RAM, NOR flash or OTP ROM is also often included on chip, as well as a small amount of RAM. Microcontrollers are designed for embedded applications, in contrast to the microprocessors used in personal computers or other general purpose applications consisting of various discrete chips.

Digital signal processor 140 may perform digital signal processing to perform a wide variety of signal processing operations. The signals processed in this manner are a sequence of numbers that represent samples of a continuous variable in a domain such as time, space, or frequency. Digital signal processing can involve linear or nonlinear operations. Nonlinear signal processing is closely related to nonlinear system identification and can be implemented in the time, frequency, and spatio-temporal domains. The application of digital computation to signal processing allows for many advantages over analog processing in many applications, such as error detection and correction in transmission as well as data compression. DSP is applicable to both streaming data and static (stored) data.

Figure 2:
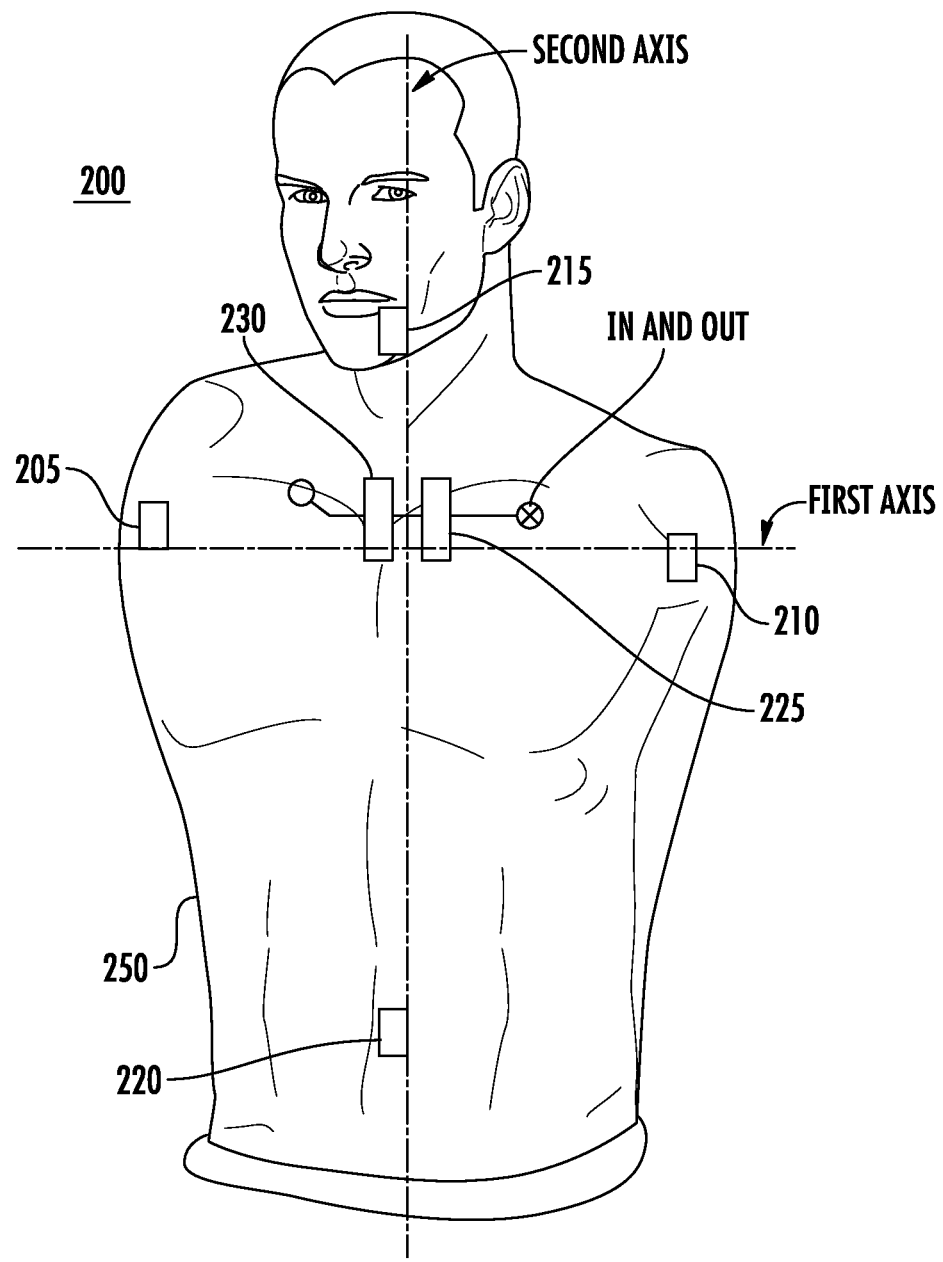
FIG. 2 illustrates a depiction of the impedance configuration using impedance pads for measuring the impedance in conjunction with the device of FIG. 1.

FIG. 2 illustrates a depiction of the impedance configuration 200 using impedance pads for measuring the impedance in conjunction with the device of FIG. 1. Configuration 200 includes a series of impedance pads configured to measure impedance in each of three axes with respect to a patient 250. A first axis first impedance pad 205 may be placed on the right side of a patient's 250 chest. Pad 205 may form an axis (first axis) (shown horizontal in FIG. 2) with a first axis second impedance pad 210 located on the left side of the patient's 250 chest.

A second impedance axis (second axis) (shown vertical in FIG. 2) may be defined by a second axis first impedance pad 215 and a second axis second impedance pad 220. Second axis first impedance pad 215 may be placed on the upper chest or throat of the patient 250. Second axis second impedance pad 220 may be located on the patient's 250 abdomen.

A third impedance axis (third axis) (shown coming in and out of page of FIG. 2) may be defined by a third axis first impedance pad 225 and a third axis second impedance pad 230. Third axis first impedance pad 225 may be placed in the center of the patient's 250 back. Third axis second impedance pad 230 may be placed in the center of a patient's 250 chest.

The present system for coordinating impedance measurements with ECG studies utilizes electrical signals transmitted from a catheter electrode (not shown in FIG. 2) to six pads 205, 210, 215, 220, 225, 230 on the patient 250 to measure the impedance. As would be understood to those familiar with an ECG procedure, the catheter electrode may be located directly in the patient's heart. For example, the catheter may be inserted internally into the patient's heart. The catheter electrode may be contained at the tip of the shaft of the catheter, for example. The catheter electrode emits burst pulses of low-frequency electrical signals, from less than 1 milliampere to 100 microamperes, which are absorbed by the six pads 205, 210, 215, 220, 225, 230 on the patient's 250 body. Generally, the use of pads 205, 210, 215, 220, 225, 230 and the catheter electrode is a unipolar measurement. The burst pulses may be of the same, or approximately the same, frequency as the signals that are measured during the ECG in order to remove any frequency error in the measurement and removal of the impedance.

By way of example only, each channel in an ECG test may be sampled 20,000 times per second with a measurement time of 1/640 seconds. This allows for approximately slightly less than 1/20000 of a second in between measurements during which time, the time multiplexing may be employed to measure the impedance. More specifically, in this example, the time between measurements may be 1/19200 seconds.

The burst pulses from the catheter may be provided when the ECG is not sampling the electrical signals from the heart. This time multiplexing avoids interference with the ECG readings. Because the system uses time multiplexing (and not frequency multiplexing), any frequency may be used for the burst pulse. This allows signals at the same or approximately the same frequency to be used to measure the impedance. The electrical signals from the heart are not sampled continuously, only sampled in multiplex. Thus, the catheter electrode may be used when the electrical signals from the heart are not being sampled. Typical values are approximately 100-200 ohms.

Figure 3:
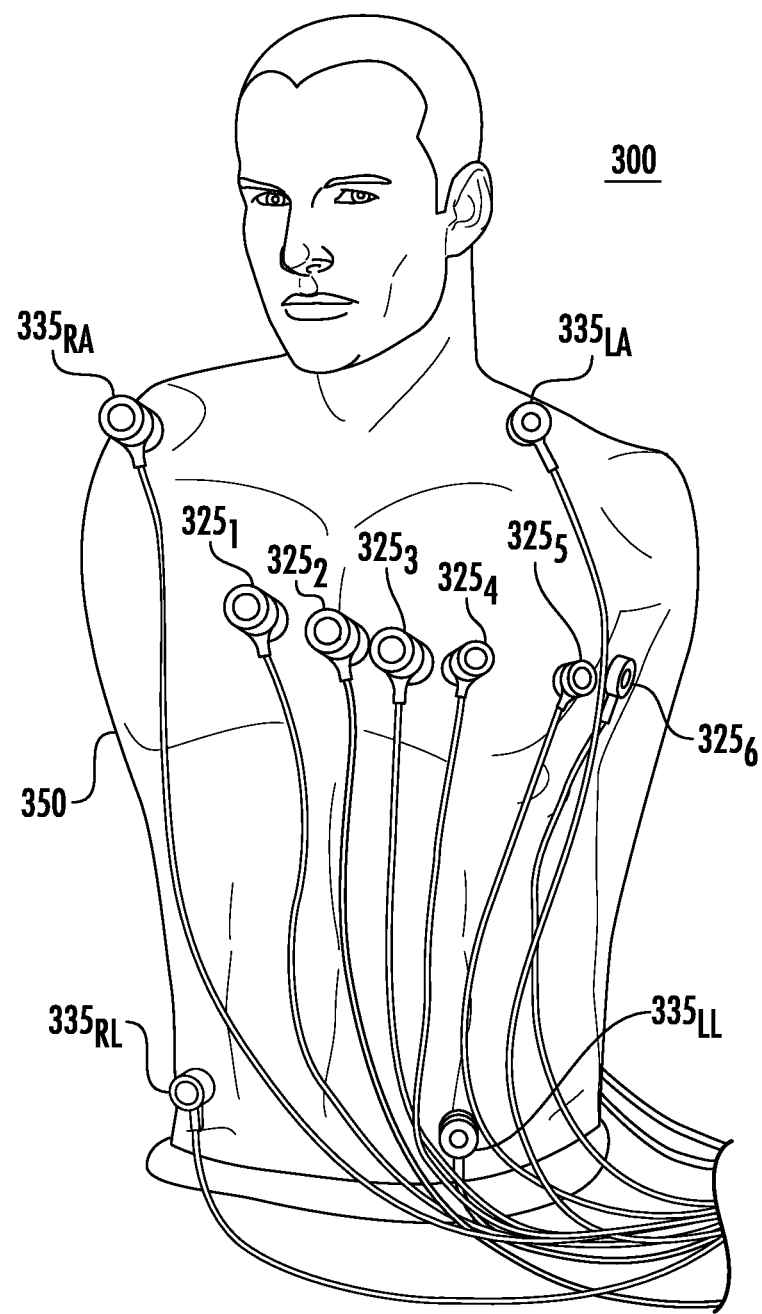
FIG. 3 illustrates a depiction of the lead configuration in conjunction with the device of FIG. 1.

FIG. 3 illustrates a depiction of the lead configuration 300 in conjunction with the device of FIG. 1. Lead configuration 300 includes a series of leads configured to measure electrical signals with respect to a patient 350. Generally, there are ten leads that are connected to specific parts of the body. The leads are of two groups: six chest leads 325 and four peripheral leads 335.

Six chest leads 325 are generally positioned with respect to the rib cage of the patient 350. The first of the chest leads $325_1$ is located near the center of the patient's 350 chest. Side lead $325_6$ is located on the side of the patient's 350 body. The other chest leads $325_2$, $325_3$, $325_4$, $325_5$ are located in between first chest lead $325_1$ side chest lead $325_6$. By way of information, chest lead $325_2$ is located at the intersection of the 4th intercostal space and the sternum of the patient 350. Chest lead $325_4$ is located in the 5th intercostal space, in line with the middle of the clavicle. Chest lead $325_3$ may be positioned midway between chest lead $325_2$ and chest lead $325_4$. Chest lead $325_5$ may be located in the 5th intercostal space in the under-arm area.

The four peripheral leads 335 may be located to capture signals at the left and right wrists and left and right legs. While referencing the signal from the arms and legs, these leads may be located on the shoulders and abdomen (as shown) or on the limbs directly. For example, lead $335_{RA}$ may be located on the right shoulder of the patient 350, lead $335_{LA}$ may be located on the left shoulder of the patient 350, lead $335_{RL}$ may be located on the lower right abdomen of the patient 350, and $335_{RL}$ may be located on the lower left abdomen of the patient 350. Individually, the leads may be utilized as described in a unipolar configuration where each leads operates alone. Such leads may be brought together and tied to a ground or the pads, for example.

Alternatively, the leads may be used in a bipolar configuration. That is, the leads may be used in a pair with the signal gathered between the leads. For example, the leads across the imaginary Einthoven triangle may be used.

Impedance may be measured by transmitting from one lead to another. Such impedance measurements may utilize the leads 325 already included on the patient's 350 body, and therefore may not require the pads shown and described with respect to FIG. 2. The measuring of impedance between two leads is referred to as a bipolar measurement of impedance.

The use of the leads in a bipolar measurement may provide the additional benefit that the leads furthest from the most recent measurement may be used to measure impedance. For example, if the electrical signals of the heart are being measured on leads 1 and 2, then the impedance may be measured on leads 16 and 17. A lead may be defined as the link between two electrodes. For example, lead 1 may be defined as being the link between leads $335_{LA}$ and $335_{RA}$, for example. Lead 2 may include the link between leads $335_{RA}$ and $335_{LL}$. Lead 3 may include the link between leads $335_{LA}$ and $335_{LL}$. One pattern that may be used is by connecting an electrode to the adjacent electrode to form the pair, for example. Other leads formed from the combinations of electrodes may also be used as would be evident to those possessing an ordinary skill in the pertinent art based on the disclosure contained herein.

During bipolar operation, the window of opportunity for making a bipolar impedance measurement at a minimum of 20 kHz sampling provides a 50 µs per electrode. In order to achieve the measurement, a multiplexer may provide a connection over which to measure the impedance between two electrodes for 3 µs. Sampling up to 200 kHz may be utilized. During a given window of opportunity only a single lead is connected while N−1 leads are not connected.

Figure 4:
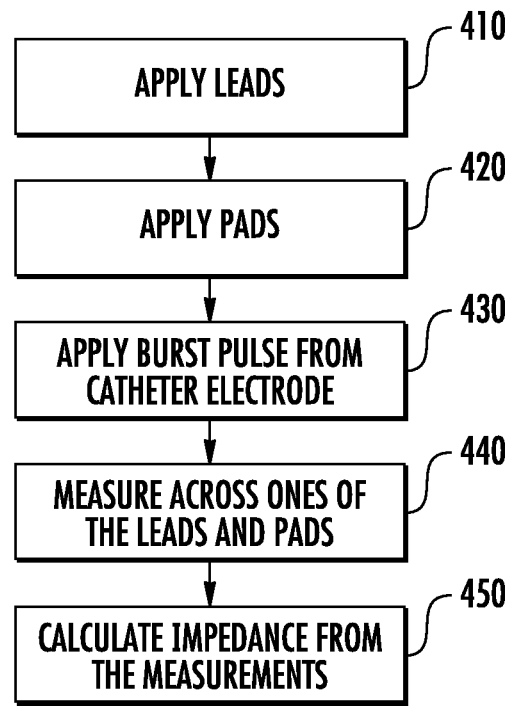
FIG. 4 illustrates a method of the present invention for measuring impedance using burst pulses in a unipolar configuration.

FIG. 4 illustrates a method 400 that may be performed in a unipolar configuration. Method 400 includes applying a plurality of leads at step 410. At step 420, method 400 includes applying a plurality impedance pads. At step 430, a unipolar impedance measurement may be performed by applying a burst pulse from the catheter electrode. A plurality of measurements may be taken across ones of the plurality of impedance pads and the plurality of leads at step 440. At step 450, the impedance for one or more leads may be determined from the plurality of measurements.

Figure 5:
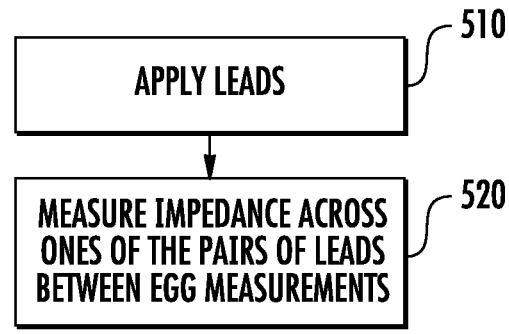
FIG. 5 illustrates a method of the present invention for measuring impedance in a bipolar configuration.

FIG. 5 illustrates a method 500 that may be performed in a bipolar configuration. Method 500 includes applying a plurality of leads at step 510. At step 520, a bipolar impedance measurement may be performed across ones of the pairs of leads between ECG measurements.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method for measuring the impedance of one or more of a plurality of leads in an electrocardiogram (ECG), the method comprising:
    applying a plurality of leads to a patient's body;
    applying a plurality impedance pads to the patient's body;
    providing a burst pulse from a catheter electrode;
    measuring impedance signals across ones of the plurality of impedance pads and the plurality of leads resulting from the provided burst pulse;
    determining the lead impedance for one or more leads from the measured impedance signals; and
    removing at least the lead impedance from the signals measured on the plurality of leads when measuring the ECG.

2. The method of claim 1 wherein the plurality of impedance pads defines an axis from the right side of the patient's chest to the left side of the patient's chest.

3. The method of claim 1 wherein the plurality of impedance pads defines an axis from the upper chest area of the patient to the lower abdomen area of the patient.

4. The method of claim 1 wherein the plurality of impedance pads defines an axis from the center of the patient's back to the center of the patient's chest.

5. The method of claim 1 wherein the plurality of leads includes a standard 12-lead ECG.

6. The method of claim 1 wherein the plurality of leads includes three limb leads.

7. The method of claim 1 wherein the plurality of leads includes three augmented limb leads arranged in a spoke fashion in the coronal plane.

8. The method of claim 1 wherein the plurality of leads includes six precordial leads configured on the perpendicular traverse plane.

9. A system for performing an electrocardiograph (ECG) and measuring impedance, the system comprising:
    a plurality of impedance pads configured to provide impedance information for the measurements;
    a plurality of leads for attaching to a subject in order to capture electric signals, the electric signals including the impedance across at least one of the plurality of leads;
    a signal processor electrically coupled to the plurality of leads to process the captured electrical signals at least by removing the impedance from the captured electrical signals; and
    an output device to output the processed captured electrical signals.

10. The system of claim 9 wherein a catheter electrode provides a burst pulse to enable the measurement of the impedance information.

11. The system of claim 9 wherein the plurality of impedance pads defines an axis from the right side of a patient's chest to the left side of the patient's chest.

12. The system of claim 9 wherein the plurality of impedance pads defines an axis from the upper chest area of a patient to the lower abdomen area of the patient.

13. The system of claim 9 wherein the plurality of impedance pads defines an axis from the center of a patient's back to the center of the patient's chest.

14. The system of claim 9 wherein the plurality of leads includes a standard 12-lead ECG.

15. The system of claim 9 wherein the plurality of leads includes three limb leads.

16. The system of claim 9 wherein the plurality of leads includes three augmented limb leads arranged in a spoke fashion in the coronal plane.

17. The system of claim 9 wherein the plurality of leads includes six precordial leads configured on the perpendicular traverse plane.

* * * * *

UNITED STATES PATENT AND TRADEMARK OFFICE
CERTIFICATE OF CORRECTION

PATENT NO. : 11,406,307 B2
APPLICATION NO. : 16/230654
DATED : August 9, 2022
INVENTOR(S) : Assaf Govari et al.

It is certified that error appears in the above-identified patent and that said Letters Patent is hereby corrected as shown below:

On the Title Page

In Item (72), under "Inventors", in Column 1, Line 2, delete "Karkur (IL)" and insert -- Pardes Hanna-Karkur (IL) --, therefor.
In Item (57), under "Abstract", in Column 2, Line 4, delete "plurality impedance" and insert -- plurality of impedance --, therefor.
In Item (57), under "Abstract", in Column 2, Line 7, delete "across ones of the" and insert -- across one of the --, therefor.

In the Specification

In Column 2, Line 46, delete "plurality impedance" and insert -- plurality of impedance --, therefor.
In Column 2, Line 48, delete "across ones of the" and insert -- across one of the --, therefor.
In Column 2, Line 64, delete "of the plurality of the" and insert -- of the --, therefor.
In Column 6, Line 38, delete "plurality impedance" and insert -- plurality of impedance --, therefor.
In Column 6, Line 41, delete "across ones of the" and insert -- across one of the --, therefor.
In Column 6, Line 48, delete "across ones of the" and insert -- across one of the --, therefor.

In the Claims

In Column 7, Line 17, in Claim 1, delete "plurality impedance" and insert -- plurality of impedance --, therefor.
In Column 7, Line 19, in Claim 1, delete "across ones of the" and insert -- across one of the --, therefor.
In Column 8, Line 4, in Claim 9, delete "electrocardiograph (ECG)" and insert -- electrocardiogram (ECG) --, therefor.

Signed and Sealed this
Nineteenth Day of September, 2023

*Katherine Kelly Vidal*

Katherine Kelly Vidal
*Director of the United States Patent and Trademark Office*